(12) United States Patent  (10) Patent No.: US 8,303,938 B2
Andersen  (45) Date of Patent: Nov. 6, 2012

(54) ANTI-CALCULUS DENTAL COMPOSITION

(76) Inventor: Douglas Andersen, San Diego, CA (US)

( * ) Notice: Subject to any disclaimer, the term of this patent is extended or adjusted under 35 U.S.C. 154(b) by 0 days.

(21) Appl. No.: 13/039,904

(22) Filed: Mar. 3, 2011

(65) Prior Publication Data

US 2011/0150789 A1  Jun. 23, 2011

Related U.S. Application Data

(62) Division of application No. 11/644,618, filed on Dec. 22, 2006.

(51) Int. Cl.
 *A61K 8/00* (2006.01)
 *A61K 8/21* (2006.01)
 *A61K 8/46* (2006.01)
(52) U.S. Cl. ................ 424/49; 424/52; 424/57
(58) Field of Classification Search ............ 424/49, 424/52, 57
 See application file for complete search history.

(56) References Cited

U.S. PATENT DOCUMENTS 4,923,684 A * 5/1990 Ibrahim et al. .......... 424/52
6,042,812 A * 3/2000 Sanker et al. .......... 424/49

OTHER PUBLICATIONS

Sam Low. American Academy of Periodontology. Chicago, IL. Jan 12, 2010 Letter.*
The Periogen Company. Daily Tartar Therapy. 2011.*

* cited by examiner

*Primary Examiner* — Frederick Krass
*Assistant Examiner* — Chris Simmons
(74) *Attorney, Agent, or Firm* — Gordon & Rees LLP; Laurie A. Axford

(57) ABSTRACT

The present invention relates generally to an anti-calculus composition and method for treating subgingival calculus. The anti-calculus composition comprises a pyrophosphate and a tripolyphosphate in a pharmaceutically acceptable carrier. The composition may also comprise a fluoride providing compound.

3 Claims, No Drawings

ANTI-CALCULUS DENTAL COMPOSITION

CROSS-REFERENCE

This application is a divisional application of U.S. patent application Ser. No. 11/644,618 filed Dec. 22, 2006, the content of which is hereby incorporated by reference in its entirety.

FIELD OF THE INVENTION

The present invention relates generally to anti-calculus compositions and methods for the treatment of a dental disease in a subject by preventing, reducing, or removing dental calculus.

BACKGROUND OF THE INVENTION

Dental Plaque

Dental plaque is a biofilm (usually a pale yellow to white color) that builds up on the surface of teeth. If not removed regularly, it can lead to dental cavities (caries) or periodontal problems (such as gingivitis). The microorganisms that form the biofilm are almost entirely bacteria (mainly streptococcus and anaerobes), with the composition varying by location in the mouth. The microorganisms present in dental plaque are all naturally present in the oral cavity, and are normally harmless. However, failure to remove plaque allows it to build up in a thick layer and leads to increased bacterial growth.

Dental Calculus

Dental plaque is a precursor of calculus. Dental calculus, or tartar, refers to a build-up of hardened (mineralized) plaque on the teeth, formed by the presence of saliva, debris, and minerals. Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of microorganisms. Its rough surface provides an ideal medium for bacterial growth, threatening the health of the gums and absorbing unaesthetic stains far more easily than natural teeth.

Calculus comes in two forms. Supragingival (outside the gums) calculus is the visible deposit that forms on the top of the teeth. Subgingival (inside the gums) calculus forms in pockets between teeth and gums. Subgingival calculus is more harmful as it facilitates faster growth of bacteria.

Buildup of calculus often causes swelling, bleeding and weakening of gums, and can lead to gum recession and tooth loss. Calculus can even extend into pockets created between the tooth and gums. The anaerobic bacteria found in pockets around teeth may be linked to cardiovascular disease and pre-term low birth weight babies. These pockets are difficult to reach by tooth brushing, and are not affected by standard mouthwashes.

Calculus accumulates in the absence of proper oral care. Once formed, it can be removed currently only by professional cleaning by a dentist or dental hygienist using a scaling procedure, which is a process involving metal scrapers to mechanically remove calculus from tooth surfaces. The mechanical dental scaling procedure may be effective in calculus removal. However, this procedure has several disadvantages. One disadvantage of dental scaling is that the process can destroy dental cementum, which is a tooth formation critical to gum/tooth attachment. Another disadvantage of dental scaling is that the treatment may remove healthy gum tissue, which cannot regenerate. Still another disadvantage is that the procedure is painful.

A variety of chemical and biological agents have also been suggested to retard calculus formation or to remove calculus after it is formed. Pyrophosphate salts and other chemical agents are known to have the ability to retard calculus formation. For example, in U.S. Pat. Nos. 4,999,184 and 4,610,871, the use of monoalkyl or dialkyl ethers of dianhydrohexitols to inhibit the formation of plaque and calculus on teeth is described. U.S. Pat. No. 4,178,363 describes the use of n-undecylenic fatty acid or a calcium or zinc salt thereof for reducing dental plaque and infections of the teeth and gums. U.S. Pat. No. 4,119,711 describes spiro 1-(hydroxyalkyl)-piperidino derivatives which have efficacy in reducing the formation of plaque. Additionally, U.S. Pat. No. 3,887,712 discloses that alexidine dihydrofluoride is useful in the treatment of dental plaque, calculus, gingivitis and related periodontal diseases. U.S. Pat. No. 4,160,821 discloses that a glycerin solution of zinc chloride or other acceptable zinc salts provides effective therapy for gingivitis when applied to the gingival and teeth. U.S. Pat. No. 4,060,600 teaches a method of treating teeth in dentistry, for the prevention of calculus, removal of caries, and dissolution of plaque, comprising applying an aqueous solution containing a hypochlorite of an alkali and/or alkaline earth metal, and an amino compound capable of forming water-soluble non-mucous irritating N-chloro and/or N-dichloro derivatives thereof to the teeth. However, all of these chemical and biological agents have some disadvantages, such as discoloration of teeth or tongue, desquamation and soreness of oral mucosa, objectionable taste, toxicity, and may also causes an imbalance of the oral flora.

Dental Pockets and Gum Disease

Calculus if not properly removed may lead to more serious dental problems such as dental pocket formation and gum disease. Calculus formations house bacteria which excrete toxins that erode periodontal ligament connections, leading to erosion of periodontal ligament connections. This erosion separates teeth from gums, forming dental "pockets." The pockets facilitate further calculus growth, leading to further separation of the teeth from the gums, ending in tooth loss.

According, there is a need for effective anti-calculus compositions and methods for the treatment of dental diseases via the non-mechanical removal of calculus from tooth surfaces, without the disadvantages that are commonly associated with conventional treatments. The anti-calculus composition of the present invention is very effective in removal of subgingival calculus, which leads to reduction of dental pockets and gum disease, and to healthier gums and prevent tooth loss.

SUMMARY OF THE INVENTION

In accordance with the present invention, an anti-calculus composition is provided for the treatment of a dental disease in a subject by preventing, reducing, or removing dental calculus. In one embodiment, the anti-calculus composition comprises two or more anti-calculus agents. The anti-calculus agents each are a polyphosphate. When the anti-calculus composition comprises two anti-calculus agents, the first anti-calculus agent is a pyrophosphate, including pyrophosphoric acid and a pharmaceutically acceptable salt thereof; the second anti-calculus agent is a tripolyphosphate, including tripolyphosphoric acid and a pharmaceutically acceptable salt thereof.

In another embodiment, the anti-calculus composition further comprises one or more pharmaceutically acceptable carriers. The anti-calculus composition may comprise a $C_2$-$C_{20}$ organic acid, such as citric acid, and bicarbonate, such as an alkali bicarbonate. The anti-calculus composition may also comprise a fluoride providing compound.

The present invention also provides a method for treating subgingival calculus using the anti-calculus composition described herein above. The method comprises the steps of applying an effective amount of a solution or suspension that contains the anti-calculus composition topically to the oral cavity of the subject, particularly to the teeth and/or gums of a subject. When the anti-calculus composition is provided in a concentrated from such as powder or a concentrated solution, the method may also include the step of preparing an application composition from the anti-calculus composition as a solution or suspension prior to the applying step.

Further, the present invention also relates to a method for treating subgingival calculus in a subgingival pocket, comprising the steps of preparing a composition comprising at least one phosphate-containing anti-calculus agent, loading the composition into an applicator device with at least one orifice, wherein the device is adapted for delivery of the composition through the orifice under pressure; and applying the composition to the subgingival pocket.

Other aspects of the invention are described throughout the specification

DETAILED DESCRIPTION OF THE INVENTION

The present invention relates generally to a dental composition and methods for the treatment of a dental disease in a subject via the prevention, reduction, and removal of dental calculus. More particularly, the present invention relates to an anti-calculus composition that is administered topically to the oral cavity of the subject Suitable topical composition includes a solution, powder, tooth paste, cream, gel or dentifrice, a mouth wash or rinse, a chewable tablet, a mouth freshener, a toothpick, a dental pack, dental floss, or other dental implements. The anti-calculus composition of the present is effective in preventing, reducing, and removing calculus, especially subgingival calculus, but without the disadvantages that are commonly associated with conventional treatments of dental diseases.

To facilitate understanding of the invention set forth in the disclosure that follows, a number of abbreviations and terms are defined below. Unless defined otherwise, all technical and scientific terms used herein generally have the same meaning as commonly understood by one of ordinary skill in the art to which this invention belongs.

The term "teeth" refers to natural teeth and any other hard surfaces, such as crowns, caps, fillings, bridges, dental implants, and the like, that are permanently fixed within the oral cavity and cleansed in situ within the oral cavity of a subject.

The term "calculus" refers to mineralized dental plaque biofilms.

The term "effective amount" refers to an amount of an agent or agents (e.g., anti-calculus agent or agents) high enough to significantly improve the condition to be treated, but low enough to avoid serious side effects (at a reasonable benefit/risk ratio), within the scope of sound medical/dental judgment. The safe and effective amount of an agent (e.g., anti-calculus agent or agents) may vary with the particular condition being treated, the age and physical condition of the patient being treated, the severity of the condition, the duration of treatment, the nature of concurrent therapy, and the particular vehicle from which the agent is applied.

The term "oral composition" refers to a topical composition that in the ordinary course of usage, is not intentionally swallowed for purposes of systemic administration of particular agents, but is rather retained in the oral cavity for a time sufficient to contact substantially the exposed dental surfaces and/or oral tissues for purposes of oral activity. The oral composition of the present invention may be in the form of a solution, toothpaste, dentifrice, tooth powder, topical oral gel, mouth rinse, mouth wash, denture product, mouthspray, lozenge, oral tablet, or chewing gum.

The term "orally-acceptable carrier" or "pharmaceutically acceptable excipient" refers to a suitable vehicle, which can be used to apply the present anti-calculus compositions to the oral cavity in a safe and effective manner. Such vehicle may include materials such as fluoride ion sources (also known as fluoride providing compounds), additional anti-calculus agents, buffers, abrasive materials, peroxide sources, alkali metal bicarbonate salts, thickening materials, humectants, water, surfactants, titanium dioxide, flavor system, sweetening agents, xylitol, coloring agents, natural saliva, and mixtures thereof.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "treating" means preventing, reducing, and/or removing dental calculus, thereby preventing, reducing and/or alleviating a dental disease.

The term "subgingival" means inside the gums. The anti-calculus composition of the present invention enters subgingival spaces or pockets, but it is understood that supragingival calculus can also be treated with the anti-calculus composition of the present invention.

Anti-Calculus Composition

The anti-calculus composition of the present invention for the treatment of a dental disease, such as subgingival calculus, comprises two or more anti-calculus agents. Suitable anti-calculus agents include, but are not limited to, polyphosphates, particularly linear molecularly dehydrated polyphosphoric acids and pharmaceutically acceptable salts thereof. The term "polyphosphate" is used herein in a broad sense, which includes a polyphosphoric acid and pharmaceutically acceptable salts thereof, wholly or partially neutralized. Non-limiting exemplary polyphosphates are trimetaphosphates, pyrophosphates, tripolyphosphates, tetrapolyphosphates, and hexametaphosphates. Similarly, those phosphate terms also include their corresponding phosphoric acid and various forms of pharmaceutically acceptable salts thereof; wholly or partially neutralized. For example, a pyrophosphate includes, but is not limited to, pyrophosphoric acid, sodium pyrophosphate, di-sodium pyrophosphates, tri-sodium pyrophosphates, tetra-sodium pyrophosphates, potassium pyrophosphate, di-potassium pyrophosphates, tri-potassium pyrophosphate, and tetra-potassium pyrophosphates. The polyphosphates employed in the present invention are all from commercial sources and are readily available from a number of chemical suppliers. In general, the anti-calculus agents each are employed in the instant anti-calculus composition in the amount from about 0.1 to about 90%, from about 1 to about 80%, or from about 2 to about 50% by weight. When the anti-calculus composition is in a concentrated form, the content of each anti-calculus agent is in the amount from about 10 to about 90%, from about 15 to about 80%, or from about 20 to about 50% by weight.

The anti-calculus composition of the present invention also includes one or more pharmaceutically acceptable carriers. In one exemplary embodiment, the anti-calculus composition comprises an alkali metal bicarbonate salt, such as sodium bicarbonate or potassium bicarbonate. Alkali metal bicarbonates are soluble in water and unless stabilized, release carbon dioxide in an aqueous solution. When supplied as a concentrated form, the anti-calculus composition contains from about 2 to about 50%, from about 10 to about 40%, or from about 15 to about 30% by weight of an alkali metal bicarbonate.

The anti-calculus composition of the present invention may also have a C2-C20 organic acid, such as citric, malic, lactic, alginic, succinic, tartaric, and ascorbic acids. When supplied in a concentrated form, the level of the $C_2$-$C_{20}$ organic acid may range in an amount from about 2 to about 50%, from about 10 to about 40%, or from about 15 to about 30% by weight.

The desired pH range of the anti-calculus composition of the present invention is between about 6 and about 9, or between about 7.5 and about 8.1. The pH of the present anti-calculus compositions is readily adjusted via buffering agents.

In an exemplary embodiment of the present invention, the anti-calculus composition comprises substantially equal amounts of tetra-potassium pyrophosphate, sodium tripolyphosphate, sodium bicarbonate, and citric acid.

In another exemplary embodiment, the anti-calculus composition comprises tetra-potassium pyrophosphate in the amount of about 37% by weight, sodium tripolyphosphate in the amount of about 37% by weight, sodium bicarbonate in the amount of about 12% by weight, citric acid in the amount of 12% by weight and sodium fluoride as a fluoride providing compound in the amount of about 0.02% by weight.

These two exemplary anti-calculus compositions are readily dissolved in water, forming an application solution to be applied topically to the oral cavity of a subject. The application solution can be readily applied using a common device such as an oral irrigator or sub-gingival oral applicator.

Formulations and Administration

The anti-calculus composition of the present invention may be formulated in various forms suitable for topical applications to the oral cavity of a subject. In one embodiment, the anti-calculus composition is formulated as a dentifrice, which is substantially solid or pasty in character, such as tooth powder, a dental tablet, a tooth paste (cream), or a dental gel. Toothpastes (creams) and gels typically contain in the topical vehicle a natural or synthetic thickener or gelling agent. Additionally, the vehicle of such solid or pasty dentifrice preparations typically contains an orally or dentally acceptable polishing material for use in conjunction with brushing of the teeth. Examples of such polishing materials are water-insoluble sodium metaphosphate, potassium metaphosphate, tri-calcium phosphate, dihydrated calcium phosphate, anhydrous di-calcium phosphate, calcium pyrophosphate, magnesium orthophosphate, tri-magnesium phosphate, calcium carbonate, aluminum silicate, zirconium silicate, silica, bentonite, and mixtures thereof. Other suitable polishing materials include the particulate thermosetting resins described in U.S. Pat. No. 4,070,510, such as melamine-, phenolic-, and urea-formaldehydes, and cross-linked polyepoxides and polyesters. Examples of polishing materials include silica gel or colloidal silica, and complex amorphous alkali metal alumino-silicates.

In another embodiment, the anti-calculus composition of the present invention is formulated as a powder, which is readily dissolved in water to form a liquid application solution. Because of their ease of administration, liquid preparations represent an advantageous oral dosage unit form. Such compositions and preparations should contain at least 0.1 percent of active compound. The percentage of the anti-calculus composition in these compositions may be varied and may conveniently be between about 1% to about 20% of the weight of the application solution.

In still another embodiment, the anti-calculus composition is provided as a liquid formulation either in a concentrated or ready-to-use form, which can be directly applied or diluted quickly prior to the application.

In one embodiment, the invention relates to a method for applying an anti-calculus composition directly to the subgingival pocket using an applicator device. Such devices include, for example, any commercially available water pick or oral irrigator, which usually have a very small (less than 100 mm, and usually less than 10 mm, and in particular between 5 and 10 mm) orifice that is designed for reaching the subgingival pocket. Such devices are also usually adapted for applying the composition under pressure so that it can be more easily applied (i.e., "squirted") in an upward direction into the subgingival pocket of the upper teeth, in addition to being applied to the subgingival pocket of the lower teeth. In this embodiment, it is also most beneficial to formulate the composition as a semi-solid or gel such that the viscosity of the composition is sufficient to allow it to stay in place in the subgingival pocket to enhance efficacy (usually more than 5,000; such as between 5,000 and 1000,000 centipoise at 20° C.)

Orally Acceptable Carrier

The orally acceptable carrier comprises one or more compatible solid or liquid filler diluents or encapsulating substances which are suitable for topical oral administration. By "compatible," as used herein, is meant that the components of the composition are capable of being comingled without interaction in a manner which would substantially reduce the composition's stability and/or efficacy.

The carriers or excipients of the present invention can include the usual and conventional components of dentifrices (including non-abrasive gels and gels for subgingival application), mouth rinses, mouth sprays, chewing gums, and lozenges (including breath mints) as more fully described hereinafter.

The choice of a carrier to be used is basically determined by the way the anti-calculus composition is to be introduced into the oral cavity. If a toothpaste (including tooth gels, etc.) is to be used, then a "toothpaste carrier" is chosen (e.g., abrasive materials, sudsing agents, binders, humectants, flavoring and sweetening agents, etc.) as disclosed in, e.g., U.S. Pat. No. 3,988,433, to Benedict. If a mouth rinse is to be used, then a "mouth rinse carrier" is chosen (e.g., water, flavoring and sweetening agents, etc.), as disclosed in, e.g., U.S. Pat. No. 3,988,433 to Benedict. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, then a "chewing gum carrier" is chosen (e.g., gum base, flavoring and sweetening agents), as disclosed in, e.g., U.S. Pat. No. 4,083,955, to Grabenstetter et al. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos. 5,198,220 and 5,242,910, issued Mar. 30, 1993 and Sep. 7, 1993, respectively both to Damani. Carriers suitable for the preparation of compositions of the present invention are well known in the art. Their selection will also depend on secondary considerations like taste, cost, and shelf stability, etc.

The anti-calculus compositions of the present invention may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The anti-calculus compositions may further comprise a fluoride providing agent (from about 0.02% to about 0.3% as fluoride ion).

Compositions of the subject invention may also be in the form of dentifrices, such as toothpastes, tooth gels and tooth powders. Components of such tooth paste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such tooth paste or tooth gel may also include one or more of an anticaries agent (from about 0.02% to about 0.3% as fluoride ion), and an anti-calculus agent (from about 0.1% to about 13%). Tooth powders, of course, contain substantially all non-liquid components.

The anti-calculus composition of the present invention may also be provided as a mouthwash, including a mouth spray. Components of such mouthwashes and mouth sprays typically include one or more of water (from about 45% to about 99%), ethanol (no greater than about 25%), a humectant (no greater than about 50%), a surfactant (no greater than about 7%), a flavoring agent (no greater than about 2%), a sweetening agent (no greater than about 3%), and a coloring agent (no greater than about 0.5%). Such mouthwashes and mouth sprays may also include a fluoride providing agent (no greater than about 0.3% as fluoride ion).

The anti-calculus composition of the present invention may be provided as dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

The anti-calculus composition of the present invention may be provided as chewing gum compositions, which typically include one or more of a gum base (from about 50% to about 99%), a flavoring agent (from about 0.4% to about 2%) and a sweetening agent (from about 0.01% to about 20%).

The anti-calculus composition of the present invention may be provided as a dental implement impregnated with the present anti-calculus composition. The dental implement comprises an implement for contact with teeth and other tissues in the oral cavity, said implement being impregnated with a composition comprising the present composition. The dental implement can be impregnated fibers including dental floss or tape, chips or strips and polymer fibers.

A medicated dental floss for controlling, reducing, removing, or preventing calculus is also contemplated. The floss incorporates the anti-calculus composition of the present invention which, as a result of the flossing action, is deposited to the inter-dental area of the teeth. Examples of making such floss are well known and are disclosed for example in U.S. Pat. No. 5,603,921.

Various other materials may be incorporated in the anti-calculus composition of the present invention such as whitening agents, preservatives, silicones, fluorine, anti-inflammatory agents, antioxidants, anti-microbial agents, anti-pain agents, chlorophyll compounds, excipients, fragrance, colorants and mixtures thereof. These adjuvants, where present, are incorporated in the preparations in amounts which do not substantially adversely affect the properties and characteristics desired.

Any suitable flavoring or sweetening material may also be employed. In the instance where auxiliary sweeteners are utilized, the present invention contemplates the inclusion of those sweeteners well known in the art, including both natural and artificial sweeteners. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like.

The anti-calculus composition of the present invention may also be used in combination with other compounds or compositions that may also be useful in the treatment or amelioration of the diseases or conditions for which the anti-calculus compositions of the present invention are useful. Such other compounds or compositions may be administered, by a route and in an amount commonly used therefore, contemporaneously or sequentially with the anti-calculus composition of the present invention.

The effective amount of the anti-calculus composition of the present invention to be employed therapeutically for the treatment of a dental disease depends on a number of factors, among which are included, without limitation, the patient's sex, weight and age, the underlying causes of the condition or disease to be treated, the formulation, and the potency of the active component.

Application

In the practice of this invention, the anti-calculus composition is applied to dental enamel and gums as by mixing with a liquid vehicle, and applied via an orally-acceptable device, such as an oral irrigator or sub-gingivital applicator. The anti-calculus composition is applied regularly to dental enamel, such as every day or every other day and preferably from 1 to 3 times daily, for at least 2 weeks up to 8 weeks or more up to lifetime. The anti-calculus composition is discharged in the rinsing process and any residual composition may linger in dental pockets, dissolving calculus, until the next composition application whereas the prior application will be rinsed away.

It should be understood that the application ranges set forth above are exemplary only and are not intended to limit the scope of this invention. The therapeutically effective amount of the anti-calculus composition may vary with factors including, but not limited to, the efficacy of the composition, stability of the composition, the severity of the conditions to be alleviated, the age and sensitivity of the subject to be treated, and the like, as will be apparent to a skilled artisan. The amount of administration can also be adjusted as the various factors change over time.

Method of Use

The present invention also relates to methods for treating a dental disease by preventing, reducing, and removing dental calculus in a subgingival pocket. The method comprises the steps of preparing a solution or suspension from the anti-calculus composition which comprises at least a pyrophosphate and polyphosphate in a pharmaceutically acceptable carrier and applying the solution or suspension to the subgingival pocket.

It should be understood that the present invention relates not only to methods for delivering the present compositions to the oral cavity of a human, but also to methods of delivering the composition to the oral cavity of other animals, e.g., household pets or other domestic animals, or animals kept in captivity.

For example, a method of use may include brushing a dog's teeth with the anti-calculus composition. Another example would include the rinsing of a cat's mouth with the anti-calculus composition for a sufficient amount of time to see a benefit. Pet care products such as chews and toys may be formulated to contain the present anti-calculus composition. The composition is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated anti-calculus composition is released into the animal's oral cavity into a salivary medium, comparable to an effective brushing or rinsing.

Therapeutic Implications

A number of clinical diseases and conditions may be treated using the anti-calculus composition of the present invention. Subjects who would benefit from treatment with the instant anti-calculus compositions include those who suffer from dental plaque; dental tartar; dental calculus; gum disease; dental pockets; dental caries; gingivitis; or periodontitis.

The present invention also involves a method for treating teeth or gums to reduce dental calculus, which comprises the step of applying to the surface of the teeth and/or gums the anti-calculus compositions of the present invention as described above. The compositions can be applied to the teeth and gums by any conventional methods, such as irrigating, brushing, spraying, painting or rinsing of the oral cavity and the like.

It has been found that the anti-calculus composition of the present invention is very effective in the treatment of subgingival calculus, in addition to supragingival calculus. As a result, subgingival inflammations, previously unmolested by prior art, have been found to be extinguished with the composition of the present invention. The subsequent reduction in inflammation provides relief to acute oral pain caused by infection. Further treatment has been found to restore healthy "pink" gum tissue to formally inflamed gums within two weeks. It has also been found that in addition to oral inflammation reduction, periodontal pocket reduction occurs in all test subjects. This process of pocket reduction is the result of both upper gum inflammation reduction, and most importantly, dental gum reattachment following subgingival calculus elimination.

The following examples are further illustrative of the nature of the present invention, but it is understood that the invention is not limited thereto. All amounts and proportions referred to herein and in the appended claims are percent by weight.

EXAMPLE

Eleven volunteer subjects with dental calculus, dental pockets with inflammation, and/or periodontal disease, with periodontal pockets, at least one periodontal pocket in excess of 5 mm, received treatment with the composition of the invention.

Treatment for 12 subjects began with ⅛ tsp. of the composition administered orally using an oral irrigator, in 500 mL of warm water, one to two times a day for 90 days. Improvements in gum inflammation were noted for all 11 subjects within 7 days as visually examined. Subjects experienced up to a 50% improvement in dental pocket depth by the end of the treatment. No periodaontal pockets increased, and all infection in every subject was arrested.

Subject 12, a 55 year old male, under the care of his personal dentist, had been in a quarterly cleaning and perio monitoring regiment for three tears prior to treatment. Periodontal surgery had been indicated prior to treatment with the composition. After a three month treatment program, subject 12's periodontal record improved from 13 bleeding sites and 21 perio sites in 10 teeth, to 7 bleeding sites and 15 perio sites in 10 teeth. After an additional three months of treatment, subject 12's periodontal record further improved to just 4 bleeding sites and 10 perio sites in 8 teeth, after which periodontal surgery was no longer indicated.

Subject 13, a 45 year old male at the time of treatment, was in addition to suffering periodontal disease, also suffering from advanced periodontal disease with pockets in excess of 8 mm. Subject 13 was experiencing multiple abscesses, bleeding and pus release with gum massage in 6 pockets. Treatment began, as above, with ⅛ tsp of the composition of the invention administered orally using an oral irrigator, in 500 mL of warm water, one to two times a day for 90 days. In addition, six pockets with in excess of 8 mm were treated with ⅛ tsp of the composition of the invention, administered orally using a subgingival applicator, in 25 mL warm water, one to two times a day for 90 days.

Subject was monitored for inflammation, swelling, infection and pocket depth every 30 days, with six pockets being recorded. As indicated in Table 1 below, this subject realized significant reduction in dental pocket depth as well as elimination of oral infection and inflammation. Prior to treatment, the subject had a deep dental pocket depth ranging from 7 to 12 mm (Table 1). After treatment for ninety days, dental pocket depth was reduced to 3 to 8 mm.

TABLE 1

Summary

| Tooth location of dental pocket | Dental Pocket Depth (mm) | | | |
|---|---|---|---|---|
| | Prior to treatment | 30 days after treatment | 60 days after treatment | 90 days after treatment |
| 22 Facial Mesial | 12 | 11 | 9 | 8 |
| 23 Facial Distal | 8 | 6 | 4 | 3 |
| 31 Facial Distal | 8 | 6 | 5 | 4 |
| 19 Facial Mesial | 11 | 9 | 7 | 6 |
| 18 Facial Distal | 10 | 9 | 8 | 8 |
| 19 Lingual Distal | 10 | 9 | 9 | 8 |

\* \* \*

The information presented above is provided to give those of ordinary skill in the art with a complete disclosure and description of how to make and use the embodiments of the invention, and is not intended to limit the scope of what the inventor regards as his invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A composition for dissolving subgingival calculus in a subgingival pocket after formation thereof comprising:
    a) a pyrophosphate consisting of tetrapotassium pyrophosphate;
    b) a polyphosphate consisting of tripolyphosphate;
    c) an alkali metal bicarbonate salt consisting of sodium bicarbonate;
    d) a C2-C20 organic acid consisting of citric acid; and
    e) a fluoride providing compound;
    wherein the composition is effective to dissolve subgingival calculus.

2. The composition of claim 1, wherein the fluoride providing compound is sodium fluoride.

3. A composition for dissolving subgingival calculus in a subgingival pocket after formation thereof comprising:
    a) from 20% to 40% by weight of tetrapotassium pyrophosphate;
    b) from 20% to 40% by weight of sodium tripolyphosphate;
    c) from 5% to 20% by weight of sodium bicarbonate;
    d) from 4% to 20% by weight of citric acid; and
    e) from 0.01 to 1% by weight of sodium fluoride;
    wherein the composition is effective to dissolve subgingival calculus.

* * * * *